United States Patent [19]

Figueras et al.

[11] 4,176,008
[45] Nov. 27, 1979

[54] METHOD, COMPOSITION AND ELEMENT FOR THE DETECTION OF NITROGEN-CONTAINING COMPOUNDS

[75] Inventors: John Figueras; Roger W. Nelson; Richard C. Sutton, all of Rochester, N.Y.

[73] Assignee: Eastman Kodak Company, Rochester, N.Y.

[21] Appl. No.: 880,828

[22] Filed: Feb. 24, 1978

[51] Int. Cl.² ............................................ G01N 33/16
[52] U.S. Cl. .................................. 435/12; 23/230 B; 23/232 R; 435/39
[58] Field of Search ............... 195/103.5 R, 103.5 U; 23/230 B, 232 R

[56] References Cited

U.S. PATENT DOCUMENTS

| | | | |
|---|---|---|---|
| Re. 27,524 | 11/1972 | Nadeau | 195/103.5 |
| 3,145,086 | 8/1964 | Free | 23/253 |
| 3,806,416 | 4/1974 | Mollering et al. | 195/62 |
| 3,873,269 | 3/1975 | Kraffczyk et al. | 23/230 B |
| 3,992,158 | 11/1976 | Przybylowicz et al. | 23/253 TP |
| 4,125,377 | 11/1978 | Gindler | 23/230 B |

OTHER PUBLICATIONS

Hantzsch, Ann. Chem. Liebigs, 215, p. 1, 1882 (translation of pp. 5-8, only).
Knoevenagel, Annalen, 281, p. 25, 1894 (translation of pp. 25-28, only).
Dunsbach. in Chemical Abstracts, vol. 66 (1967), 82993a.

Primary Examiner—Lionel M. Shapiro
Attorney, Agent, or Firm—D. M. Schmidt

[57] ABSTRACT

Methods, compositions and elements for detecting a nitrogen-containing compound capable of releasing ammonia upon enzymatic action are described. The method comprises contacting in an aqueous medium a sample suspected of containing such a compound and a novel assay composition comprising at least one enzyme which catalyzes the decomposition of the compound to ammonia and detecting the ammonia by condensation with a diketone and measuring the color or fluorescence produced by the resulting dihydropyridine.

The foregoing assay composition can be incorporated into single-layer or multilayer analytical elements of the type known in the prior art. A preferred such element comprises an isotropically porous spreading layer in fluid contact with a reagent layer. The spreading layer is most preferably non-fibrous.

25 Claims, 4 Drawing Figures

METHOD, COMPOSITION AND ELEMENT FOR THE DETECTION OF NITROGEN-CONTAINING COMPOUNDS

BACKGROUND OF THE INVENTION

1. Field of the Invention

The present invention relates to novel methods, compositions, and elements for detecting nitrogen containing compounds capable of releasing ammonia upon enzymatic action.

2. Description of Related Art

There are several standard methods for the determination of urea. The Berthelot reaction utilizes the conversion of urea to ammonium carbonate by the action of urease followed by an oxidative condensation of ammonia with phenol catalyzed by sodium nitroprusside to form a blue indophenol. The condensation of diacetyl (or an oxime thereof) with urea in an acidic solution may be employed to produce a yellow diazine. In the Nesslerization procedure, urea is hydrolyzed by urease as in the Berthelot reaction and the ammonia produced is reacted with mercuric iodide and potassium iodide to yield (presumably) $NH_2Hg_2I_3$ (red). A titrimetric procedure may be used in which urea is hydrolyzed by urease and the ammonia titrated with HCl to a Bromcresol green-methyl red endpoint. Urea concentration may also be determined potentiometrically by the immersion of an $NH_4^+$ sensitive electrode in a solution containing urea and urease. Finally the ammonia produced by the action of urease upon urea may be coupled with α-ketoglutaric acid in the presence of L-Glutamate:NAD oxoreductase (deaminating), E.C. 1.4.1.2 and nicotinamide adenine dinucleotide, reduced form, to yield L-glutamate and the oxidized form of the coenzyme. The reaction is followed at 340 nm.

The condensation reaction involving two equivalents of a β-diketone and one each of ammonia and formaldehyde was first described by A. Hantzsch, *Ann. Chem. Liebigs,* 215, 1 (1882). Its only clinical usage has apparently been in the detection of glycerides in which liberated glycerol is oxidized to formaldehyde and condensed with 2,4-pentanedione and an ammonium salt to yield the tetra-substituted dihydropyridine. This procedure was reported by F. Dunsbach, *Z. Klin. Chem.,* 4, 262 (1966) (N.B. CA 66:82993a). No suggestion is made to use this reaction to detect analyte other than glycerides.

The condensation reaction involving one equivalent of a β-diketone and one of ammonia was described by E. Knoevenagel, *Annalen,* 281, 25 (1894). No suggestion is made of using this reaction to detect analyte other than ammonia.

U.S. Pat. No. Re 27,524 reissued Nov. 28, 1972 describes a process for measuring the amount of a nitrogen-containing compound in a sample, the enzyme being reactive with the nitrogen-containing compound which process comprises:

(1) mixing the sample with a compound that is enzymatically reactive with ammonia;

(2) adding to the nitrogen-containing compound an amount of enzyme sufficient to release ammonia at a measurable rate; and (3) measuring the rate of reaction of ammonia with the compound that is enzymatically reactive with ammonia. The only compound reactive with ammonia which is specifically disclosed is β-nicotinamide-adenine dinucleotide.

Creatinine has been detected as described in U.S. Pat. No. 3,806,416 issued Apr. 23, 1974 by converting creatinine to creatine using creatinine amidohydrolase and subsequently converting creatine to sarcosine and urea using creatine amidinohydrolase. As described below, this pair of reactions can be coupled to the instant urea assay to provide an assay for creatinine.

U.S. Pat. No. 3,992,158 issued Nov. 16, 1976 to Przybylowicz and Millikan describes unique integral elements for use in the qualitative and quantitative analysis of liquids such as blood serum and urine, which elements preferably comprise a porous spreading layer in fluid contact or communication with a reagent layer which comprises at least one material interactive with a component or decomposition product of a component of the liquid. This patent does not describe specifically compositions of the type described herein.

U.S. Pat. No. 3,145,086 describes a diagnostic composition for the determination of abnormally high blood urea, preferably impregnated on a cellulose strip, which composition combines urease with an indicator system including a buffer and an indicator material capable of changing color in the presence of a pH change. There is no suggestion of the use of urease in combination with a β-diketone capable of condensing with ammonia and formaldehyde.

U.S. Pat. No. 3,873,269 describes a diagnostic composition for the determination of urea, preferably impregnated on an absorbent carrier such as filter paper, which combines urease with an indicator system capable of changing color in the presence of a pH change. There is no suggestion of the use of urease in combination with a diketone capable of condensing with ammonia.

Commonly-owned U.S. application Ser. No. 688,446 filed on May 20, 1976, U.S. Pat. No. 4,066,403, issued Jan. 3, 1978, entitled "Improved Multilayer Analytical Element" by B. Bruschi, describes a dry element having at least two reagents for generating a measurable indication of the presence of BUN, and a barrier composition separating the two reagents, the composition being selectively permeable to a decomposition product which will react with one of the reagents. Nowhere is there a specific disclosure that diketones should be one of the reagents, and the barrier layer would prevent the proper functioning of the present invention.

RELATED APPLICATIONS

This application is related to concurrently filed U.S. patent application Ser. No. 880,827 of Frank et al., entitled "Method, Composition and Element for the Detection of Nitrogen-Containing Compounds," which discloses contacting in an aqueous medium a sample and a novel composition comprising an enzyme which catalyzes the decomposition of nitrogen-containing compounds to ammonia, and detecting the ammonia with a β-diketone and formaldehyde or a formaldehyde source.

SUMMARY OF THE INVENTION

Figure 1:
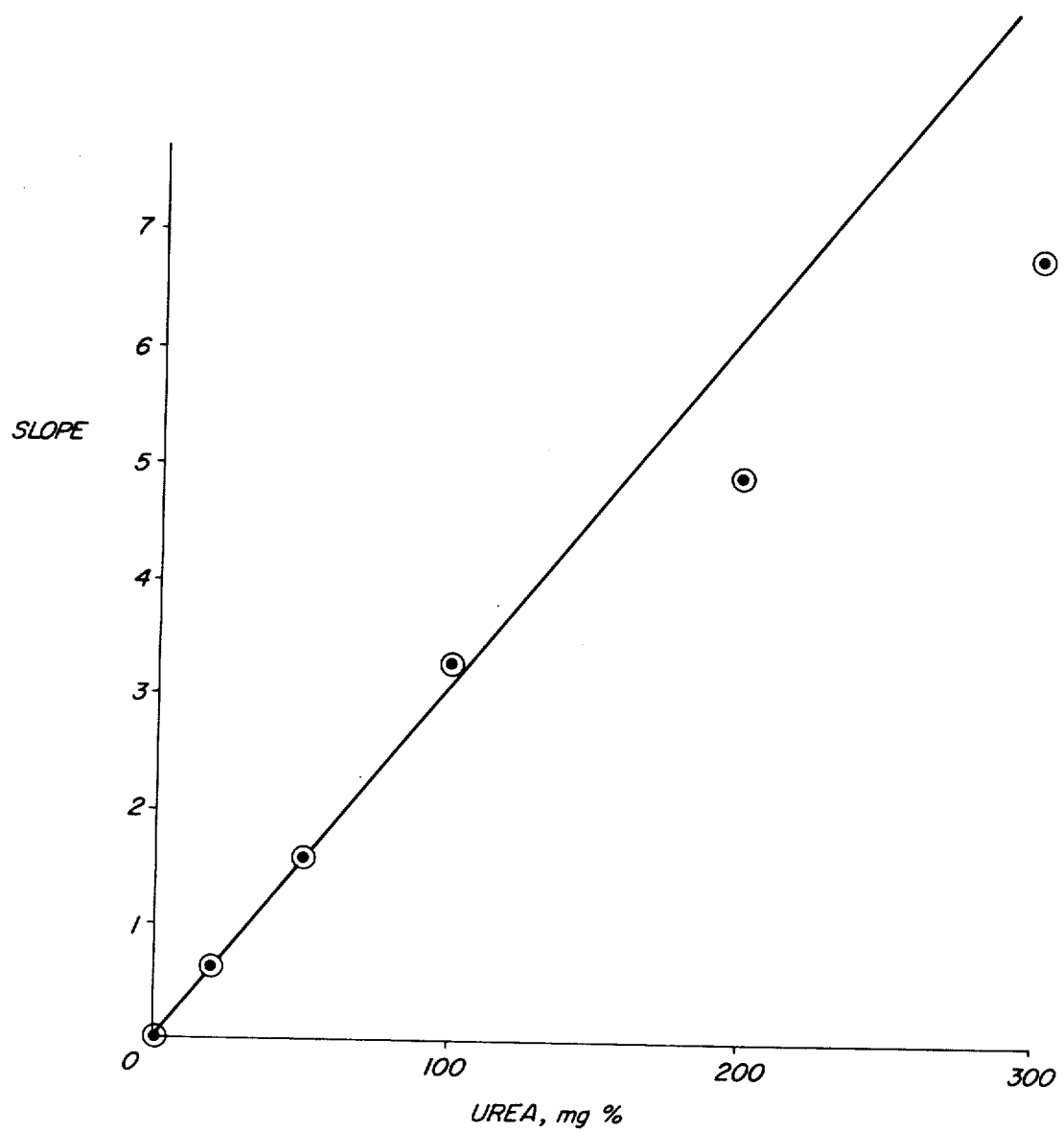
FIGS. 1–4 are plots of the slope of output curves of elements of the invention against urea concentration in mg/dl.

The compositions and elements of the present invention provide a means for detecting nitrogen-containing compounds via the formation of dihydropyridines. The reagents may be used in the form of aqueous solutions, reconstitutable powders or dry, single or preferably multilayer analytical elements.

As used herein, the term analyte refers to nitrogen-containing material which releases ammonia either directly on interaction with one or more enzymes or indirectly by the action of two or more enzymes which act sequentially on the analyte and on at least one decomposition product of the analyte.

According to the present invention, the ammonia may be present in a sample solution as ammonia or obtained in situ from analyte present in the solution sample by any of a variety of known enzyme catalyzed decompositions which result in the formation of ammonia. The ammonia is condensed with an appropriate diketone (as described hereinafter), to produce a spectrophotometrically detectable dihydropyridine whose concentration can be related to the concentration of nitrogen-containing analyte present in the sample. The assay may be performed kinetically.

According to the present invention there is provided a composition for the detection of nitrogen-containing analyte in an aqueous sample said composition comprising at least one enzyme which catalyzes the decomposition of the analyte to ammonia, and a diketone of the formula

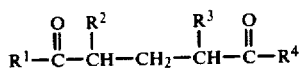

wherein $R^1$, $R^2$, $R^3$ and $R^4$ are the same or different, and are each hydrogen, aryl of from 6 to 20 carbon atoms, a straight- or branched-chain alkyl or aralkyl of from about 1 to about 20 carbon atoms, or a cycloalkyl of from about 5 to about 7 carbon atoms. An analytical element containing said composition is also described.

The preferred dry multilayer analytical element described herein comprises a spreading layer in fluid contact with a reagent layer containing the above-mentioned reagent system. The various materials are disposed within the element so that ammonia released by the action of at least one enzyme on analyte present within a liquid sample applied to the surface of the element is condensed with the diketone. Optionally, the element may include a support.

DESCRIPTION OF PREFERRED EMBODIMENTS

The present invention involves novel methods, compositions and elements for detecting nitrogen-containing analyte capable of releasing ammonia upon enzymatic action in biological or other complex aqueous fluids. The procedure in simplified form may also be used for the detection of ammonia or ammonium ion. The preferred mode of detection relies upon the fluorescence of the condensed dihydropyridine.

Although the disclosure herein will be directed primarily to the determination of urea as analyte using urease as the enzyme which releases ammonia from the analyte, it should be apparent that numerous other analytes may be similarly determined. For example, creatinine can be determined using the methods and compositions described herein when the creatinine decomposition reactions are those described, for example, in U.S. Pat. Nos. 3,806,416, 3,907,644 and 3,912,588 wherein the nitrogen-containing creatinine is converted to urea by the following reactions:

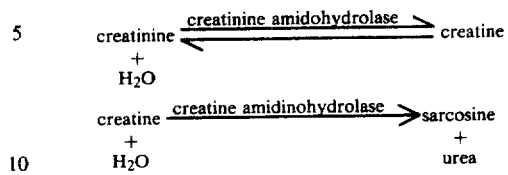

The urea is then determined by the method described herein.

Table I provides a listing of other nitrogen-containing compounds that can be determined by the procedure of this invention and enzymes which can be used in the ammonia-releasing reaction. After determining specific optimum conditions of temperature, ionic strength, etc., and a linear portion in a curve is obtained by plotting the rate of change in fluorescence versus nitrogen concentration, the procedures for all the determinations become identical and could be readily understood by reference to the examples presented herein.

Table I

| Parent compound | Enzyme |
| --- | --- |
| l-Lysine | l-Lysine amino acid oxidase |
| l-Histidine | Histidine-a-deaminase |
| l-Serine | l-Serine dehydrase |
| l-Threonine | l-Threonine amino acid oxidase |
| l-Homoserine | l-Homoserine amino acid oxidase |
| l-Cysteine | l-Cysteine amino acid oxidase |
| Glycine | Glycine oxidase |
| l-Aspartic acid | l-Aspartase |
| Quinine | Quinine deaminase |
| Aliphatic amines | Monoamine oxidase |
| d-Amino acids | d-Amino acid oxidase |
| l-Glutanine | l-Glutaminase |

The general chemical reactions in a total process of this invention are as follows:

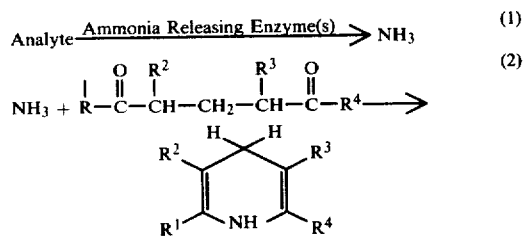

wherein each of $R^1$, $R^2$, $R^3$ and $R^4$ independently is hydrogen, an aryl group of from about 6 to about 20 carbon atoms, a straight- or branched-chain alkyl, or aralkyl group having from about 1 to about 20 carbon atoms, or a cycloalkyl group of from about 5 to about 7 carbon atoms.

Equation (1) presents the decomposition of analyte to ammonia in the presence of a suitable enzyme. Reaction (2) shows the condensation of a diketone with one equivalent of ammonia to form a dihydropyridine This reaction sequence extends the pyridine synthesis described by E. Knoevenagel at *Annalen*, 281, 25 (1894) to clinical usages.

In the determination of urea reaction (1) would be

The formation of the condensation product can be monitored spectrofluorimetrically to give a measure of the ammonia consumed in equation (2) and, therefore, a measure of the nitrogen and consequently the analyte present in the original sample. The wavelength of absorption and emission of the product is dependent on the structure of the dihydropyridine formed and consequently the diketone used in the reaction sequence chosen.

The urea assay described herein can, for the convenience of the user, be utilized in different physical formats. The reactants can be prepared in aqueous solution and used to determine the analyte content of a sample immediately on hand. In addition, these solutions can be divided into quantities convenient for the user, freeze-dried according to conventional techniques, and stored for later reconstitution and use. In a further, preferred embodiment, a "dry" single or multilayer analytical element can be prepared containing, in one or more layers, optionally on a support, all the reactants required for the determinations described herein. Analytical elements of these types which comprise "bibulous" materials impregnated or otherwise incorporating reagents or so-called integral multilayer elements which include layers to meter, spread, filter, etc. sample applied thereto are well known in the art.

Each of the above formats provides an accurate, convenient method for the assay of nitrogen-containing analyte using the formation of a dihydropyridine detectable by spectrofluorimetric techniques from a diketone and the ammonia released by the sample when contacted with appropriate enzyme(s).

Solution Assay

The use of the reaction sequence described hereinabove in a solution assay employs techniques commonly known in the art. The necessary reagents are described hereinbelow:

The enzyme Urea amidohydrolase (E.C. 3.5.1.5), commonly termed urease, is a highly specific enzyme catalyzing the decomposition of urea to ammonia. The enzyme may be obtained from bacterial sources such as *B. pasteurii* or from jack bean. The optimum pH of the enzyme varies from about 6.0 to 7.0 depending on the source. Urease is highly stable unless too highly purified, and has a useful life of about 6 to 12 months when stored at 4° C. Activity for urease is generally stated in Sumner Units (SU) where one SU of urease activity is that quantity of urease which will form 1 mg of ammonia nitrogen from urea in phosphate buffer, pH 7.0 at 20° C. in 5 minutes. The concentration of urease in the solution assay should be sufficiently high to rapidly convert the urea available in a given sample to ammonia. Activities of urease from about 100 SU/l to about 1000 SU/l are practical.

The carbon dioxide formed in the initial reaction is not further required for the determination of the urea and does not interfere in any way with the reactions involved in the total process.

In the determination of other analytes, as described hereinabove, other ammonia releasing enzyme(s) are substituted for the urease and the useful concentrations, pH optimums, etc. therefor are readily determinable by the skilled artisan.

The diketone used in reaction (2) is of the formula:

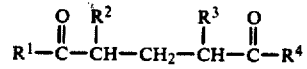

wherein each of $R^1$, $R^2$, $R^3$ and $R^4$ independently is hydrogen, an aryl group having from about 6 to about 20 carbon atoms in the ring structure, a straight- or branched-chain alkyl, for example, methyl, ethyl, propyl, T-butyl, etc., or aralkyl group having from about 1 to about 20 carbon atoms, for example, phenyl, naphthyl, etc., or a cycloalkyl group of from about 5 to about 7 carbon atoms, for example, cyclopentyl, cyclohexyl, etc.

A specific example of a compound of this structure is methylenebis(acetoacetic ester), which forms, for example, with $NH_3$, 2,6-dimethyl-3,5-dicarbethoxy-1,4-dihydropyridine. This condensation product fluoresces at a wavelength of about 451–475 nm. Another useful diketone is 2,4-pentanedione.

The diketone should be chemically pure and is preferably used at a concentration of from about 1 to about 3 weight percent of the solution and preferably at about 1.5 weight percent. The concentration of the ester being limited by the concentration of buffer salts in the reaction mixture.

An acid buffer system is employed containing about 0.5 to about 2.5 weight percent of a buffer such as acetic acid, citric acid or the like followed by adjustment of pH with a base such as sodium hydroxide to a pH of from about 5.5 to about 6.5 and preferably from about 5.9 to about 6.1. The acid buffered system has the advantage of operating within the optimum pH range of the enzyme urease.

In use the nitrogen-containing analyte is detected by contacting in an aqueous medium a liquid suspected of containing the analyte and a reagent composition comprising diketone and enzyme or enzymes which catalyze the release of ammonia from the analyte for a period sufficient to obtain fluorescence from which a rate or endpoint determination of ammonia concentration and consequently analyte concentration can be made. In the assay of blood serum for urea the unknown sample and the reagent composition are preferably contacted at a temperature of between about 37° and about 60° C. for up to about 5 minutes. In such a determination a preferred volume ratio of test sample to reagent solution is from about 1:5 to about 1:50.

Analytical Elements

The preferred analytical elements of the present invention simplify greatly the assay of liquids for nitrogen-containing analyte. Using these elements such an assay requires no reagent mixing and can be automated to permit rapid determination of nitrogen-containing analyte with a minimum of laboratory technician participation.

Thus, according to a preferred embodiment of the present invention the foregoing reagents are incorporated into an integral element for the detection of nitrogen-containing analyte in aqueous liquids. The element comprises a spreading layer in fluid contact with a reagent layer and contains interactive materials comprising:

(a) enzymes which catalyze the release of ammonia from nitrogen-containing analyte; and (b) an ammonia detection composition comprising a diketone which can condense with ammonia to form a dihydropyridine.

The interactive materials are disposed within the element so that nitrogen-containing analyte in a liquid sample applied to the element releases ammonia to produce, in the element, a detectable change that is related, preferably quantitatively, to the analyte content of the liquid sample. Optionally, the element may include a support.

Other than the diketone, which is always most preferred in the reagent layer, the interactive materials which accomplish release of ammonia are preferably incorporated into the element as follows:

(I) all in the reagent layer; or
(II) all in the spreading layer.

The analytical elements described herein will be referred to primarily as elements for the determination of urea and nitrogen-containing analyte; however, it should be clear that they are similarly useful for the determination of enzymes which release ammonia from analytes and for ammonia per se.

Integral analytical elements having a spreading layer and a reagent layer are described in U.S. Pat. No. 3,992,158 issued Nov. 16, 1976, to E. P. Przybylowicz and A. G. Millikan.

The preferred elements described herein are of this type and comprise:

(1) a spreading layer which serves to deliver a uniform apparent concentration of analyte to;
(2) a reagent layer in fluid contact with the spreading layer; and
(3) optionally, a support.

The various enzymes and other interactive materials which serve to release ammonia from analyte contained in a liquid sample applied to the spreading layer and to provide detectable changes related to the analyte content of the liquid, are incorporated into one or more layers of the element.

Reference herein to fluid contact between a spreading layer and a reagent layer in an integral analytical element identifies the ability of a fluid, whether liquid or gaseous, to pass in such element between superposed regions of the spreading layer and the reagent layer. Stated in another manner, fluid contact refers to the ability to transport components of a fluid between the layers in fluid contact. Although such layers in fluid contact can be contiguous, they may also be separated by intervening layers as described hereinafter. However, layers in the element that physically intervene a spreading layer and reagent layer in mutual fluid contact will not prevent the passage of fluid between the fluid contacting spreading and reagent layers.

The Spreading Layer

As used herein, the term spreading layer refers to a layer, isotropically porous or otherwise, that can accept a liquid sample, whether applied directly to the spreading layer or provided to it from a layer or layers in fluid contact with the spreading layer, and which distributes (i.e., meters) within the layer the solvent or dispersion medium of the sample and at least one dissolved or dispersed component such that a uniform concentration of such component is provided at the surface of the spreading layer facing the reagent layer(s) of the element. It should be understood that the uniformity of such concentration is a uniformity as measured by techniques such as those described hereinafter. As such, the uniform concentration can also be termed a uniform apparent concentration. (The spreading layer is synonymously referred to herein as the metering layer.) In the context of this invention, the spread component will, of course, include analyte present in the applied sample. It will be appreciated that such an apparent concentration can be achieved with concentration gradients present through the thickness of or otherwise in the spreading layer. Such gradients do not present any difficulty to obtaining quantitative test results and can be accommodated using known calibration techniques.

The spreading layer can be an isotropically porous layer. Reference herein to isotropic porosity identifies the fact of substantial porosity in all directions within the spreading layer. It will be understood that the degree of such porosity may be variable, if necessary or desirable, for example, regarding pore size, percentage of void volume or otherwise. It shall be understood that the term isotropic porosity (or isotropically porous) as used herein should not be confused with the terms isoporous or ionotropic often used with reference to filter membranes to signify those membranes having pores that are continuous between membrane surfaces. Likewise, isotropic porosity should not be confused with the term isotropic, used in contradistinction to the term anisotropic, which signifies filter membranes having a thin "skin" along at least one surface of the membrane. See, for example, *Membrane Science and Technology*, James Flinn Ed, Plenum Press, New York (1970).

As will be appreciated, the extent of spreading is dependent in part on the volume of liquid to be spread. However, it should be emphasized that the uniform apparent concentration obtained with spreading is substantially independent of liquid sample volume and will occur irrespective of the extent of spreading. As a result, elements of this invention generally do not require precise sample application techniques. However, a particular liquid sample volume may be desirable for reasons of preferred spread times or the like. Because the elements of this invention are able to produce quantitative results using very small sample volumes that can be entirely taken up within a conveniently sized region of the spreading layer (e.g., one square centimeter), there is no need to remove excess moisture from the element after application of a liquid sample. Further, because spreading occurs in the spreading layer and the spread component is provided to the fluid contacting reagent layer without apparent substantial lateral hydrostatic pressure, there is not the "ringing" problem often seen with prior analytical elements when soluble reagents were used.

The spreading layer need only produce a uniform concentration of spread component per unit area at its surface facing a reagent layer with which the spreading layer is in fluid contact, and it is very convenient to determine whether a particular layer can be suitable for spreading purposes by means of the simple test described in the aforementioned Przybylowicz and Millikan U.S. Pat. No. 3,992,158. Other useful materials for and concerning the spreading layer are described in aforementioned U.S. Pat. No. 3,992,158, the contents of which are expressly incorporated herein by reference.

Isotropically porous layers can be prepared using a variety of components. In one aspect, particulate material can be used to form such layers, wherein the isotropic porosity is created by interconnected spaces between the particles.

The Reagent Layers(s)

Reagent layer(s) in the elements of this invention are desirably permeable, preferably uniformly permeable, and optionally porous if appropriate, to components spreadable within the metering or spreading layer. As used herein, the term permeability includes permeability arising from porosity, ability to swell or any other characteristic. Such layers generally include a matrix in which is distributed, i.e., dissolved or dispersed, the enzymes and other reagents interactive with analyte or decomposition products of analyte and ammonia. Interactive materials are discussed hereinafter.

The distribution of interactive materials (i.e., enzymes and other reagents) can be obtained by dissolving or dispersing them in the matrix material. Although uniform distributions of interactive materials are often preferred, they may not be necessary if the interactive material is, for example, an enzyme which is not consumed in any reaction but only serves as a catalyst which is continuously reused.

Desirably, reagent layers are uniformly permeable to spread components. Uniform permeability of a layer refers to permeability such that, when a homogeneous fluid is provided uniformly to a surface of the layer, measurements of the concentration of such fluid within the layer, made with identical equipment and under identical conditions but through different regions of a surface of the layer, will yield (i.e., be capable of yielding) substantially equal results. By virtue of uniform permeability, undesirable concentration gradients within, for example, a reagent layer as described herein, are avoided.

The choice of a matrix material for the reagent or registration layers described herein is, of course, variable and dependent on the intended method of use of the element as well as the particular interactive materials which are incorporated therein as described hereinafter. Desirable matrix materials can include hydrophilic materials including both naturally occurring substances like gelatin, gelatin derivatives, hydrophilic cellulose derivatives, polysaccharides such as dextran, gum arabic, agarose and the like, and also synthetic substances such as water-soluble polyvinyl compounds like poly(vinyl alcohol) and poly(vinyl pyrrolidone), acrylamide polymers, etc. Organophilic materials such as cellulose esters and the like can also be useful, and the choice of materials in any instance will reflect the use parameters for any particular element. For example, if a reagent which degrades gelatin is used, gelatin is not a particularly suitable reagent matrix. To enhance permeability of the reagent layer, if not porous, it is often useful to use a matrix material that is moderately swellable in the solvent or dispersion medium of liquid under analysis.

In addition to its permeability, the reagent layer is desirably substantially free from any characteristic that might appear as or contribute to mottle or other noise in the detection of an analytical result produced in an integral element of the invention. For example, variations in color or in texture within the reagent layer, as may occur when fibrous materials such as papers are used as a permeable medium, may be disadvantageous due to non-uniform reflectance or transmittance of detecting energy, e.g., when the detectable change has occurred in and is detected in the reagent layer. Also, although fibrous materials like filter and other papers are highly permeable overall, they typically exhibit widely ranging degrees of permeability between regions of the paper, for example, based on structural variations such as fiber dimensions and spacing. As a result, such materials are not considered uniformly permeable and, as such, although useful, are not preferred in either the spreading or reagent layers of the preferred embodiments of the present invention. It should be appreciated that the use of fibrous constituents, such as in appropriate combination with the non-fibrous materials, may be desirable.

Interactive Materials

The enzymes and other interactive materials used in the elements of the present invention are described hereinabove.

The concentrations of the components of the various interactive materials useful in the elements described herein are dependent to a large extent upon the concentration of analyte in the sample under test, the sophistication of the detection apparatus, the detectable product produced, etc., and are readily determinable by the skilled artisan. Typical values are shown in Table II and the examples below.

Table II below provides a ready reference for the generally useful and preferred concentration ranges of the various components of the novel assay compositions described herein.

Table II

| Interactive Material | Generally useful ranges | Preferred ranges |
|---|---|---|
| urease | 10,000–30,000 $\mu/m^2$ | 15,000–23,000 $\mu/m^2$ |
| diketone | 2–4 g/m$^2$ | 2.5–3.5 g/m$^2$ |

Of course useful results may be obtained outside of these ranges; however, these have generally been found useful and preferred in methods and elements as described herein.

In the foregoing Table II, one international unit of enzyme is defined as that quantity of enzyme which results in the conversion of one micromole of substrate in one minute at 37° C. and pH 7.

As is well recognized in the art, all enzymes possess a pH-activity profile, i.e., a graphic representation of variations in the activity of the enzyme with varying pH.

Thus, it is readily apparent that it is generally desirable to buffer the layer(s) of the elements described herein which contain the respective reagents at pH levels which optimize the activity of contained enzymes. Techniques for achieving this type of buffering are well known in the art and involve dissolving or dispersing suitable concentrations of buffer in the compositions which are subsequently dried to form the layered element. Suitable buffers for buffering to preselected pH levels are described in detail by Good in *Biochemistry* 5, 467 (1966). Particularly preferred buffers are discussed hereinabove.

Supports

The integral analytical elements of the present invention can be self-supporting or the spreading layer, reagent layer and any other associated layers can be coated on a support. Useful support materials, when such are used, include paper and polyolefin coated paper, as well as a variety of polymeric materials such as cellulose acetate, poly(ethylene terephthalate), polycarbonates and polyvinyl compounds such as polystyrenes, etc.

The support can be opaque or it can transmit light or other energy depending, of course, on the mode of detection used. A support of choice in any case will be compatible with the intended mode of result detection. Preferred supports include transparent support materials capable of transmitting electromagnetic radiation of a wavelength within the region between about 200 nm and about 900 nm. The support need not, of course, transmit over the entire 200-900 nm region but must transmit in the region of the indicating radiations. When an element includes a support, the reagent layer is interposed in the element between the support and the spreading layer. Specifically preferred transmission ranges for elements of the present invention will be apparent from the discussion of the various preferred indicator compositions discussed above. When used, supports having thicknesses of between about 1 and about 10 mils have been found satisfactory, although the thickness can vary broadly depending on such factors, for example, as the intensity of the detecting radiation and the sensitivity of the detecting apparatus.

Other Layers

The element may incorporate a distinct registration layer which contains no reagents but receives dihydropyridine produced in the reagent or spreading layer and holds it for detection.

The analytical element of the present invention is preferably adapted for use in an analytical system employing reflection techniques of spectrophotometric or spectrofluorometric analysis, and consequently generally includes a layer which functions as a reflecting layer and thereby provides a suitable background measurement of detectable product through the support side of the element. The reflecting layer will permit the passage of analyte and/or decomposition products of analyte to the reagent layer, and should provide an effective background for reflection spectrophotometry. A white background is generally preferred for this purpose. In view of its function as a background for indicator formed in the reagent or registration layer, any reflective layer will normally intervene the spreading and reagent or registration layers. Such a layer may, however, intervene a reagent and registration layer where such structure is appropriate. Reflectance can be provided by a layer also serving, for example, as a spreading layer or it can be provided by an additional layer that may not have an additional function within the element. Pigments, such as titanium dioxide and barium sulfate, are reflective and can be used to advantage in a reflecting layer. Blush polymers can also constitute a suitable reflecting material. As can be appreciated, pigment spreading layers may be useful for this purpose as can blush polymer layers that may also be spreading layers. In one preferred aspect, blush polymer layers can also incorporate a pigment to enhance spreading and/or reflectivity. The amount of pigment that can be included in a layer together with blush polymer is highly variable, and amounts of from about 1 to about 10 parts by weight of pigment per part by weight of blush polymer are preferred, with from about 3 to about 6 parts pigment per part of blush polymer being most preferred.

Filtering layers may also be present in the element. The composition and preparation of such layers are well known in the art and, when present, they serve to remove from the sample components which could interfere with the indicating reaction or otherwise hinder the determination. Thus, in the use of the multilayer analytical elements for analysis of analyte in whole blood, a separate filtering layer could serve to remove red blood cells while transmitting the serum to the layer below. In the analysis of blood serum or other fluids, the filtering layer may serve to remove unwanted components which could hinder or confuse the primary indicating reaction. The aforementioned blush polymer layers may also, under certain circumstances, serve as filtering layers. If the element is to be used for analysis of whole blood, it is desirable that any filtering layer have a pore size of from about 0.5 to about 5 microns.

Element Preparation

Integral analytical elements of the type described herein may be prepared in accordance with the methods and techniques described in aforementioned U.S. Pat. No. 3,992,158.

The ammonia releasing enzyme or enzymes can be incorporated into the reagent layer. However, according to a highly preferred embodiment of the present invention, such interactive material is incorporated into the spreading layer, for example, by dispersing the enzymes in a lyophilized state in the coating medium used to form the spreading layer, and then coating this mixture over the reagent layer. According to this embodiment, spreading of the sample and release of ammonia are accomplished substantially simultaneously and the ammonia transmitted to the reagent layer. Such a configuration utilizes the time needed to spread the sample to prepare it for immediate reaction with the ammonia detection reagents in the reagent layer. As another alternative, a distinct layer which includes the ammonia releasing enzyme or enzymes may be incorporated between the spreading layer and the reagent layer to accomplish ammonia release before the sample reaches the ammonia detection reagents but after spreading is complete.

Wherever the enzymatic ammonia releasing material is incorporated, the layer should be buffered, if at all possible, to optimize the enzyme activity. In the case of an element for the detection of urea wherein urease is used as the ammonia releasing enzyme, the layer should be buffered at a pH of between about 4.8 and about 9.5. The pH optima for other ammonia releasing enzymes are, of course, readily determinable and layers containing same should be appropriately buffered.

A preferred embodiment of the integral elements hereof uses a reagent layer prepared by modifying an assay solution described hereinabove with a binder such as gelatin and solvent such as water and coating such a solution into a layer and drying. Such a layer comprises from about 30 to about 50 weight percent binder, from about 20 to about 30 weight percent of diketone, from about 10,000 to about 30,000 u/m$^2$ urease and from about 15 to about 25 weight percent of buffer.

As all of the layers described herein are preferably formed by coating from solutions or dispersions are described in the aforementioned Przybylowicz and Millikan application, it is often necessary to include coating aids which impart uniform coating properties to the layers.

Whatever coating aids are used for this purpose, it is important that they do not inhibit or interfere with any of the enzymes or reagents present in any of the various layers. Particularly useful coating aids include nonionic surfactants such as the octyl phenoxy polyethoxy ethanols commercially available from Rohm and Haas Company under the Triton tradename (X-100, 102, 165, 305 and 405 being particularly useful), p-nonylphenoxy(-polyglycidol) commercially available from Olin Mathieson Corporation under the tradename Surfactant 10G, and polyethylene glycols such as the Carbowax materials available from Union Carbide. Of course, surfactants which are useful as hydrolysis stimulators may also serve as coating aids which improve the coating characteristics of the materials in manufacture. When used as coating aids, concentrations of surfactant on the order of between about 0.05 and about 10 percent by weight have been found useful. Preferred concentration ranges for surfactants as coating aids range between about 0.5 and about 2% by weight.

In addition to coating aids, the element may include small amounts of other addenda such as preservatives, e.g., ethylenediamine tetracetic acid (about 1% by weight) or dithiothreitol (about 0.5% by weight), etc.

Use of the Element

In use, as demonstrated by the examples which follows, a sample usually on the order of from about 5 to about 50 μl is applied to the spreading or other outermost layer of the element. It is usually applied as a contact spot or free drop, using known application techniques and apparatus. In passage through the spreading layer the sample drop is spread and is then delivered to the underlying reagent layer. Also during passage through the spreading layer or the reagent layer, depending upon the embodiment used, analyte contained in the applied sample releases ammonia on contact with the appropriate enzyme(s) which ammonia is finally detected by measurement of increased levels of fluorescence. This increase in fluorescence can be quantified and related to the ammonia released and consequently the concentration of analyte in the sample. The measurement of absorbance using an excitation energy of 412 nm and detecting emissions at 490 nm has proven practical and effective for many of the dihydropyridines useful with this invention.

The element can be held at a constant temperature in the range from about 30° to about 60° C. while monitoring the reaction. The assay method does not require complete reaction and can be done kinetically.

The following examples are included to illustrate further the present invention.

EXAMPLE 1

Elements for the determination of blood-urea-nitrogen (BUN) were prepared according to the following general format. It is noted that these elements have a separate layer, under the reagent layer, comprising a hardenable polymeric buffer.

Elements were prepared by coating layers as described on a cellulose acetate support:

| Layer 1 | |
|---|---|
| copoly(acrylic acid-co-N-(m-hydroxyphenyl)methacrylamide) 95 wt. % acrylic acid | 10.8 g/m$^2$ |
| bis(vinylsulfonylmethyl) ether | 0.11 g/m$^2$ |
| (melt adjusted to pH 6.0 prior to coating) | |
| Layer 2 | |
| agarose | 5.40 g/m$^2$ |
| Na$_2$HPO$_4$ | 1.62 g/m$^2$ |
| citric acid | 1.08 g/m$^2$ |
| methylenebis(acetoacetic ester) | 3.24 g/m$^2$ |
| copoly[styrene-co-N-vinylbenzyl-N,N-dimethylbenzyl-ammonium chloride-co-divinylbenzene] | 2.16 g/m$^2$ |
| octylphenoxy polyethoxy ethanol (triton X-100 available from Rohm and Haas Co.) | 0.13 g/m$^2$ |
| urease | 22,680 μ/m$^2$ |
| (melt adjusted to pH 6.0 prior to coating) | |
| Layer 3 | |
| poly(n-isopropylacrylamide) | 0.32 g/m$^2$ |
| Layer 4 | |
| cellulose acetate | 6.6 g/m$^2$ |
| titanium dioxide | 46.0 g/m$^2$ |
| Estane 5711 (a polyurethane elastomer, available from B. F. Goodrich) | 1.38 g/m$^2$ |
| octylphenoxy polyethoxy ethanol (Triton X-405 available from Rohm and Haas Co.) | 2.69 g/m$^2$ |

Figure 2:
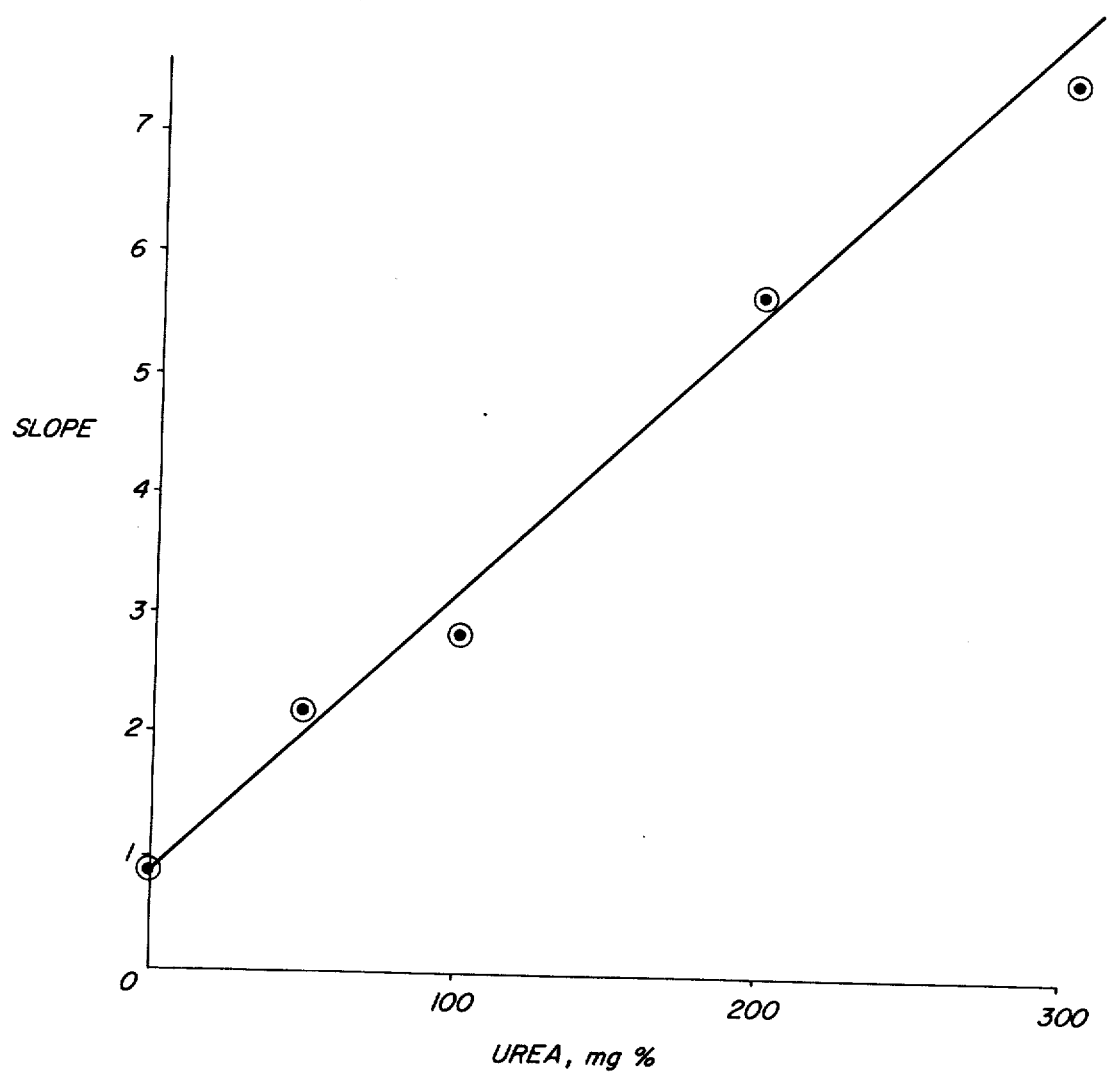

The coated elements were evaluated by spotting with aqueous standards and with spiked blood serum standards. The samples were monitored (fluorescene-vs.-time) in a filter fluorimeter standardized to 250 mv vs. BaSO$_4$. The sample chamber was maintained at a temperature of 42° C. Plots of the slope of the straight line portions of the output curves against urea concentration were then prepared (see FIGS. 1 and 2). The calibration curves thus obtained demonstrate excellent linearity up to 100 mg/dl urea with the aqueous standards and good linearity up to 300 mg/dl added urea with the spiked serum.

The coated element was then evaluated for change in response with change in serum pH over a range of 6.7 to 8.4. Table I shows the ph response for a serum spiked with 200 mg/dl urea in terms of slope and in terms of apparent urea concentration as read from a calibration curve.

Table I

| Serum pH | Slope | Urea Equivalents |
|---|---|---|
| 6.7 | 5.58 | 204 |
| 7.8 | 5.70 | 208 |
| 8.4 | 5.60 | 204 |

As is shown above, the coating shows very little change in response with change in serum pH over a range of 6.7 to 8.4

EXAMPLE 2

Analytical Element for Urea Assay

Figure 3:
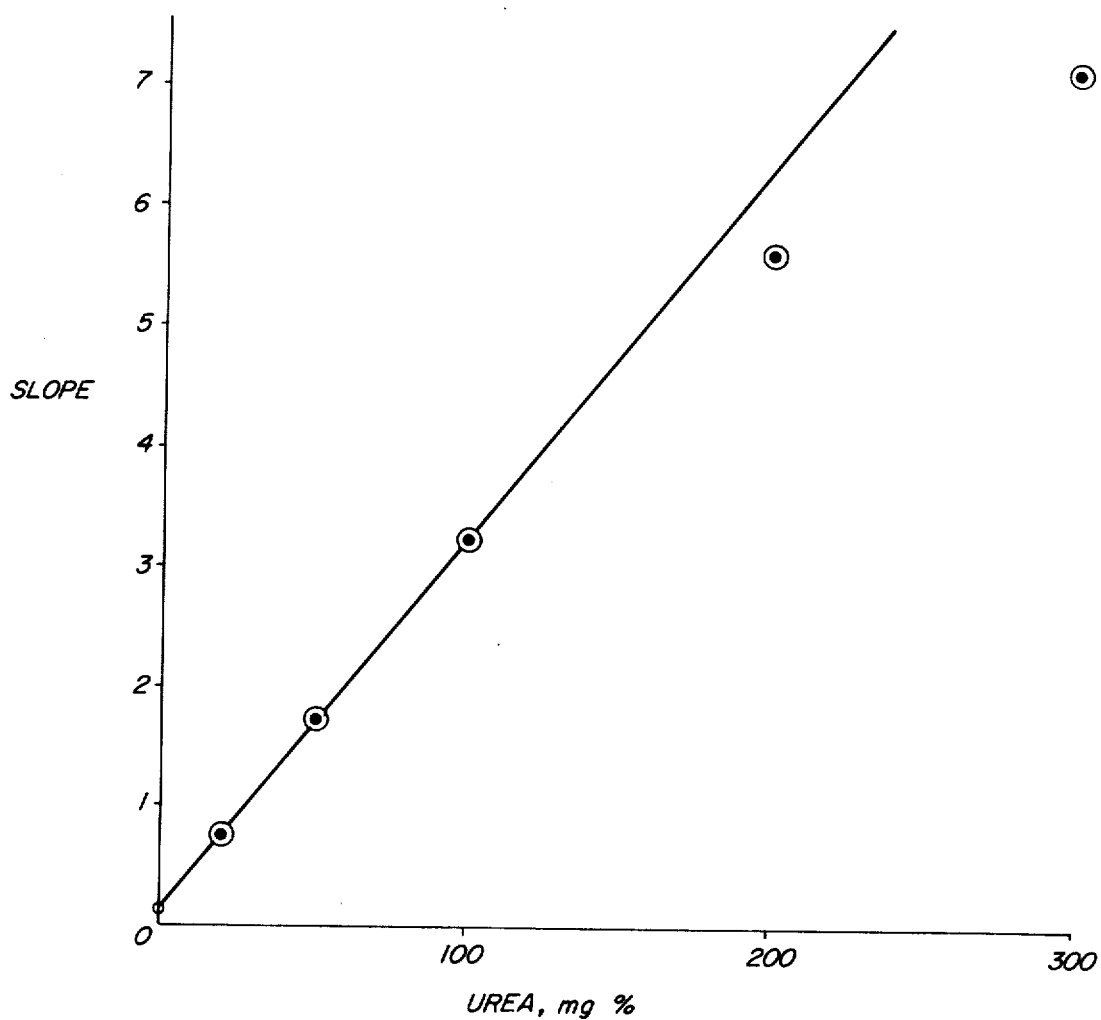
Figure 4:
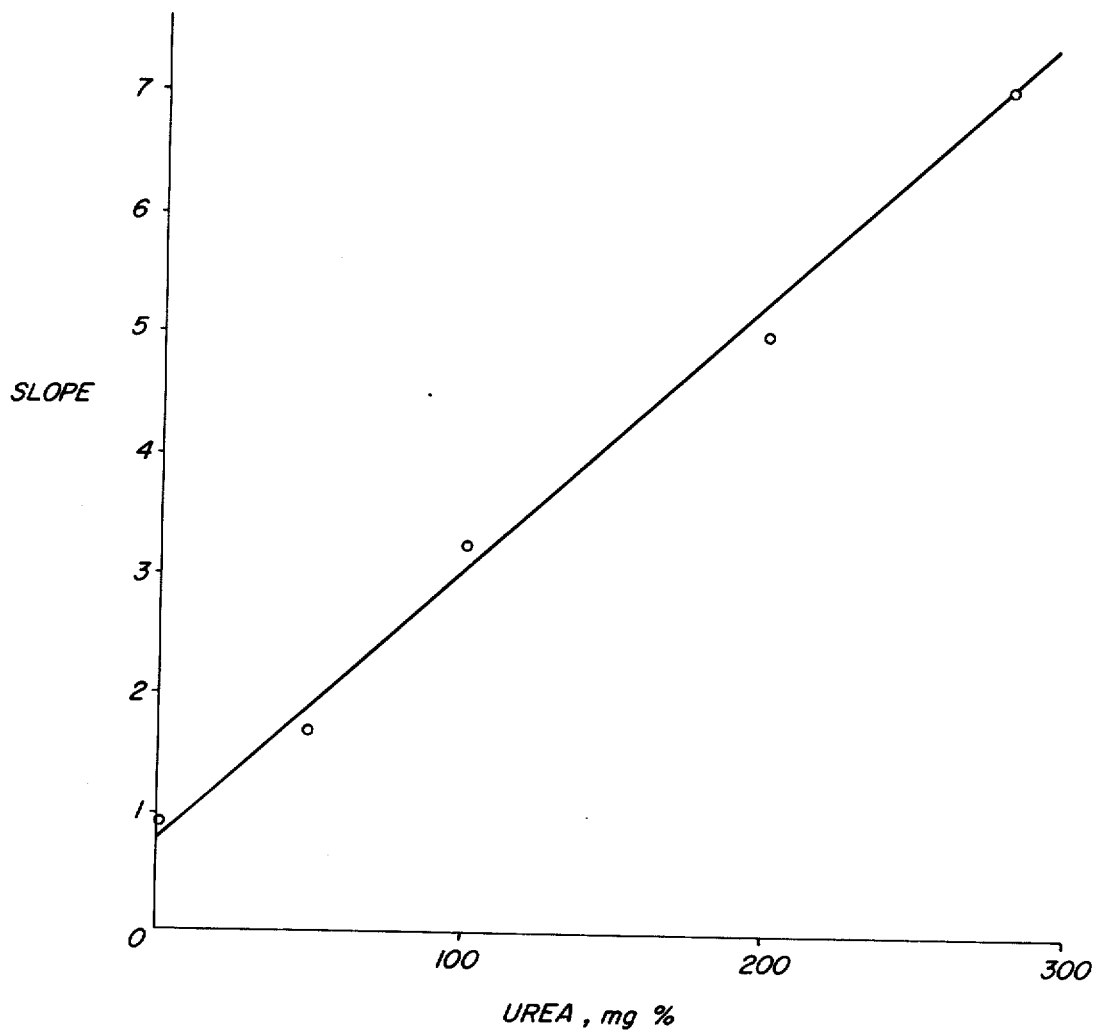

An analytical element for the detection of urea was prepared as in Example 1 with the following exception. In Layer 2 the agarose was replaced with deionized gelatin (10.8 g/m$^2$) and bis(vinylsulfonylmethyl ether) (0.05 g/m$^2$). The element was evaluated as in Example 1. Plots of the slope of the straight line portions of the output curves against urea concentration demonstrate excellent linearity up to 100 mg/dl urea with the aqueous standards and good linearity up to 300 mg/dl added urea with the spiked serum. (See FIGS. 3 and 4). Uniform response to serum pH change was also demonstrated as follows:

Table II

| Serum pH | Slope | Urea Equivalents |
|---|---|---|
| 6.7 | 5.28 | 194 |
| 7.8 | 5.45 | 200 |
| 8.4 | 5.30 | 1.94 |

Thus, in terms of slope and in terms of urea concentration read from a calibration curve, there was little change in response with change in serum pH over the given range.

ALTERNATE EMBODIMENTS

As should be apparent to the skilled artisan, the reagent compositions described herein can also be incorporated into the myriad of analytical elements described in the art, including those using at least one "bibulous" layer which has been impregnated in one way or another with a reagent composition which produces a detectable change on contact with appropriate analyte. Elements of this kind incorporating reagent compositions as described herein are intended to be within the scope of the appended claims. Such elements are structurally described, for example, in the following U.S. patents: U.S. Pat. Nos. 2,912,309, 3,092,465, 3,349,006, 3,099,605, 3,811,840, 3,881,993, 3,901,657, 3,552,928, 3,607,093, 3,798,004, 3,802,848.

The invention has been described in detail with particular reference to certain preferred embodiments thereof, but it will be understood that variations and modifications can be effected within the spirit and scope of the invention.

We claim:

1. An element for the determination in an aqueous sample of nitrogen-containing analyte capable of releasing ammonia upon enzymatic action, said element comprising a spreading layer and a reagent layer in fluid contact and containing (a) at least one enzyme which catalyzes the decomposition of the analyte to ammonia, and (b) a diketone of the formula

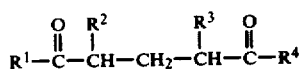

wherein R$^1$, R$^2$, R$^3$ and R$^4$ are the same or different, and are each hydrogen, aryl of from 6 to 20 carbon atoms, a straight- or branched-chain alkyl or aralkyl of up to about 20 carbon atoms, or a cycloalkyl of from about 5 to about 7 carbon atoms.

2. The element of claim 1 further comprising a buffer.

3. The element of claim 1 further comprising a buffer to maintain the pH of the composition between about 4.5 and about 6.5.

4. The element of claim 2 wherein the buffer maintains the pH at from about 5.9 to about 6.1.

5. The element of claim 2 wherein the buffer is selected from the group consisting of acetic acid and citric acid.

6. The element of claim 1 wherein the diketone is methylenebis(acetoacetic ester).

7. The element of claim 1 wherein the enzyme is urease.

8. A composition for the detection in an aqueous sample containing analyte capable of releasing ammonia upon enzymatic action, said composition comprising at least one enzyme which catalyzes the decomposition of the analyte to ammonia, and a diketon of the formula

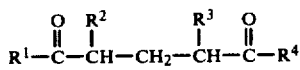

wherein R$^1$, R$^2$, R$^3$ and R$^4$ are the same or different, and are each hydrogen, aryl of from 6 to 20 carbon atoms, a straight- or branched-chain alkyl or aralkyl of up to about 20 carbon atoms, or a cycloalkyl of from about 5 to about 7 carbon atoms.

9. The composition of claim 8 further comprising a buffer.

10. The composition of claim 8 further comprising a buffer to maintain the pH of the composition between about 4.5 and about 6.5.

11. The composition of claim 9 wherein the buffer maintains the pH of the composition at from about 5.9 to about 6.1.

12. The composition of claim 9 wherein the buffer is selected from the group consisting of acetic acid and citric acid.

13. The composition of claim 8 wherein the diketone is methylenebis(acetoacetic ester).

14. A composition for the detection of urea in an aqueous sample said composition comprising urease and a diketone of the formula

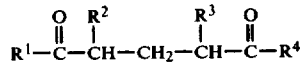

wherein R$^1$, R$^2$, R$^3$ and R$^4$ are the same or different, and are each hydrogen, aryl of from 6 to 20 carbon atoms, a straight- or branched-chain alkyl or aralkyl of up to about 20 carbon atoms, or a cycloalkyl of from about 5 to about 7 carbon atoms.

15. The composition of claim 14 further comprising a buffer.

16. The composition of claim 14 further comprising a buffer to maintain the pH of the composition at a pH of between 4.5 and about 6.5.

17. The composition of claim 16 wherein the buffer maintains the pH of the composition at from about 5.9 to about 6.1.

18. The composition of claim 15 wherein the buffer is selected from the group consisting of acetic acid and citric acid.

19. The composition of claim 14 wherein the diketone is methylenebis(acetoacetic ester).

20. A method for the detection of nitrogen-containing analyte capable of releasing ammonia upon enzymatic action comprising the steps of:
(a) contacting in an aqueous medium a sample suspected of containing such analyte and an assay composition comprising at least one enzyme which catalyzes the decomposition of the analyte to ammonia and a diketone of the formula

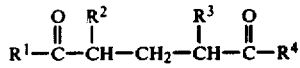

wherein $R^1$, $R^2$, $R^3$ and $R^4$ are the same or different and are each hydrogen, aryl of from 6 to 20 carbon atoms, a straight- or branched-chain alkyl or aralkyl of up to about 20 carbon atoms, or a cycloalkyl of from about 5 to about 7 carbon atoms; and
(b) detecting any color or fluorescence produced in step (a).

21. The method of claim 20, wherein said composition further comprises a buffer.

22. The method of claim 20, wherein said composition further comprises a buffer to maintain the pH of the composition at a pH of between about 4.5 and about 6.5.

23. The method of claim 20 wherein said composition further comprises a buffer to maintain the pH of the composition at from about 5.9 to about 6.1.

24. The method of claim 21 wherein the buffer is selected from the group consisting of acetic acid and citric acid.

25. The method of claim 20 wherein the diketone is methylenebis(acetoacetic ester).

* * * * *